United States Patent
Meißner et al.

(10) Patent No.: US 10,519,102 B2
(45) Date of Patent: Dec. 31, 2019

(54) METHOD FOR PREPARATION OF AMMONIA GAS AND $CO_2$ FOR A UREA SYNTHESIS PROCESS

(71) Applicant: ThyssenKrupp AG, Essen (DE)

(72) Inventors: Christoph Meißner, Dortmund (DE); Denis Krotov, Dortmund (DE); Olaf von Morstein, Essen (DE); Matthias Patrick Krüger, Herne (DE)

(73) Assignee: THYSSENKRUPP AG, Essen (DE)

( * ) Notice: Subject to any disclaimer, the term of this patent is extended or adjusted under 35 U.S.C. 154(b) by 0 days.

(21) Appl. No.: 15/103,875

(22) PCT Filed: Dec. 11, 2014

(86) PCT No.: PCT/EP2014/003315
§ 371 (c)(1),
(2) Date: Jun. 12, 2016

(87) PCT Pub. No.: WO2015/086149
PCT Pub. Date: Jun. 18, 2015

(65) Prior Publication Data
US 2016/0318855 A1    Nov. 3, 2016

(30) Foreign Application Priority Data
Dec. 12, 2013    (DE) .................. 10 2013 113 980

(51) Int. Cl.
*C07C 273/04* (2006.01)
*C07C 273/10* (2006.01)
(Continued)

(52) U.S. Cl.
CPC .......... *C07C 273/04* (2013.01); *B01D 53/047* (2013.01); *C01B 3/025* (2013.01);
(Continued)

(58) Field of Classification Search
CPC .......... C07C 273/04; C01B 3/12; C01B 3/56; C01B 3/025; C01B 2203/042;
(Continued)

(56) References Cited

U.S. PATENT DOCUMENTS 2,852,344 A * 9/1958 Kolbel .................... C01B 3/025
                                                    423/362
3,327,487 A    6/1967 Karwat
(Continued)

FOREIGN PATENT DOCUMENTS

CN    102101643    *  6/2011
CN    102101644 A    6/2011
(Continued)

OTHER PUBLICATIONS

Machine generated English language translation of Park, KR 2011007613, Jul. 6, 2011, p. 1-9.*
(Continued)

*Primary Examiner* — Amy C Bonaparte
(74) *Attorney, Agent, or Firm* — Lathrop Gage L.L.P.

(57) ABSTRACT

The invention relates to a process for preparing ammonia gas and $CO_2$ for urea synthesis. In the process of the invention, a process gas containing nitrogen, hydrogen and carbon dioxide as main components is produced from a metallurgical gas. The metallurgical gas consists of blast furnace gas, or contains blast furnace gas at least as a mixing component. The process gas is fractionated to give a gas stream containing the $CO_2$ component and a gas mixture consisting primarily of $N_2$ and $H_2$. An ammonia gas suitable for the urea synthesis is produced from the gas mixture by means of ammonia synthesis. $CO_2$ is branched off from the $CO_2$-containing gas stream in a purity and amount suitable for the urea synthesis.

9 Claims, 1 Drawing Sheet

(51) Int. Cl.
*C10B 3/02* (2006.01)
*C01C 1/04* (2006.01)
*C21B 5/06* (2006.01)
*B01D 53/047* (2006.01)
*C01B 3/12* (2006.01)
*C01B 3/56* (2006.01)
*C01B 3/02* (2006.01)

(52) U.S. Cl.
CPC ............... *C01B 3/12* (2013.01); *C01B 3/56* (2013.01); *C01C 1/0488* (2013.01); *C07C 273/10* (2013.01); *C21B 5/06* (2013.01); *B01D 2258/025* (2013.01); *C01B 2203/0283* (2013.01); *C01B 2203/042* (2013.01); *C01B 2203/0475* (2013.01); *C01B 2203/068* (2013.01); *C01B 2203/1258* (2013.01)

(58) Field of Classification Search
CPC ...... C01B 2203/068; C01B 2203/0283; C01B 2203/043; C01B 2203/047; C01B 2203/0475; C01B 2203/1205; B01D 53/047; B01D 2257/7027; B01D 2258/025; B01D 2257/504; B01D 2257/30; B01D 2257/7022; C01C 1/0488; C01C 1/02; C01C 1/04; C01C 1/0405; Y02P 20/52; Y02P 10/122; Y02P 10/283; Y02P 20/152; Y02P 10/143; C21B 5/06; C21B 7/002; C21B 2100/00; C21B 2100/02

See application file for complete search history.

(56) References Cited

U.S. PATENT DOCUMENTS

| | | | |
|---|---|---|---|
| 3,872,025 A | | 3/1975 | Singleton |
| 4,013,454 A | * | 3/1977 | Jordan ............... C01B 3/12 423/359 |
| 5,523,483 A | | 6/1996 | Singh et al. |
| 6,190,632 B1 | * | 2/2001 | Shah ............... C01B 3/025 423/352 |
| 6,986,800 B2 | * | 1/2006 | Duarte-Escareno .... C21B 5/008 75/458 |
| 2008/0245101 A1 | * | 10/2008 | Dubettier-Grenier ...... F25J 3/04181 62/636 |

FOREIGN PATENT DOCUMENTS

| | | | |
|---|---|---|---|
| CN | 103303863 | * | 9/2013 |
| DE | 3101067 A1 | | 7/1982 |
| DE | 3335087 A1 | | 4/1985 |
| EP | 1031534 A1 | | 8/2000 |
| FR | 2494711 | * | 5/1982 |
| GB | 288154 A | | 7/1929 |
| GB | 298190 A | | 12/1929 |
| GB | 586650 | * | 3/1947 |
| JP | 2002161303 | * | 6/2002 |
| JP | 2002161303 A | | 6/2002 |
| KR | 20110076103 | * | 7/2011 |
| RU | 2254331 C1 | | 6/2005 |
| RU | 2283832 C2 | | 9/2006 |
| SU | 1064863 A3 | | 12/1983 |

OTHER PUBLICATIONS

Machine generated English language translation of Huang, CN 103303863, Sep. 18, 2013, p. 1-16.*
English language translation of Park (KR 20110076103, Jul. 6, 2011), p. 1-20.*
Topham ("Carbon Dioxide" Ullmann's Encyclopedia of Industrial Chemistry, 2000, p. 647-666) (Year: 2000).*
Chen ("An evaluation of hydrogen production from the perspective of using blast furnace gas and coke oven gas feedstocks" International Journal of Hydrogen Energy, vol. 36, 2011, p. 11727-11737) (Year: 2011).*
PCT Application No. PCT/EP2014/03315, International Search Report dated Jun. 18, 2015, 7 pages.
PCT Application No. PCT/EP2014/03315, Written Opinion dated Jun. 18, 2015, 10 pages.
Meessen ("Urea" Ullmann's Encyclopedia of Industrial Chemistry, 2010, p. 657-695).
U.S. Appl. No. 15/472,558, Non-Final Office Action dated Dec. 27, 2017, 34 pages.
U.S. Appl. No. 15/472,558, Final Office Action dated Oct. 16, 2018.
Russian Application No. 2016127978, Office Action dated Jun. 27, 2018.

* cited by examiner

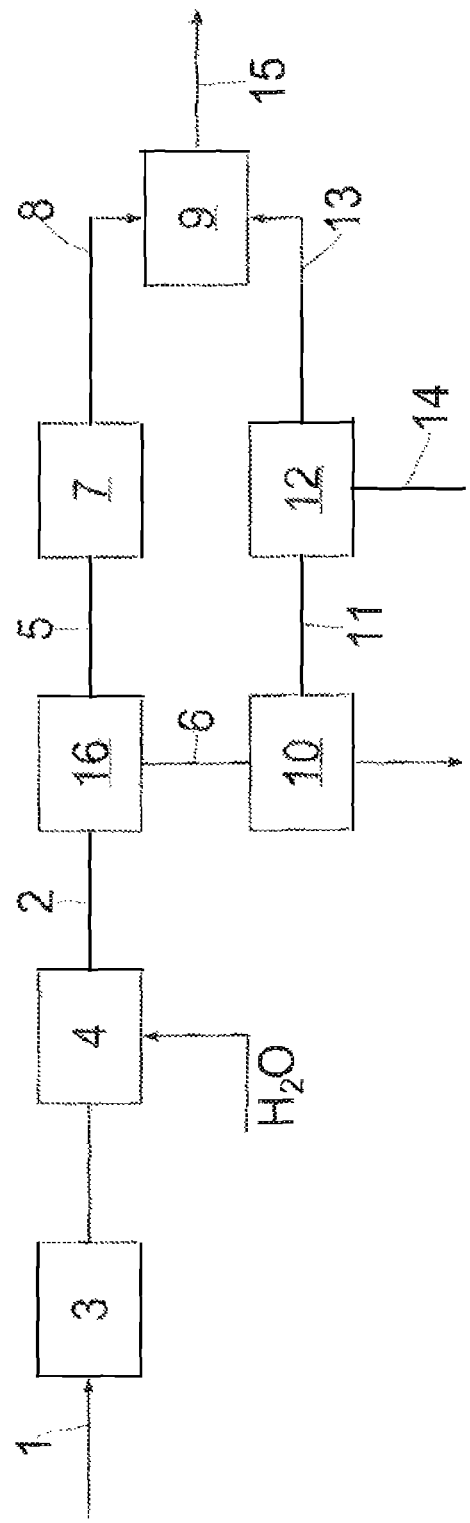

METHOD FOR PREPARATION OF AMMONIA GAS AND $CO_2$ FOR A UREA SYNTHESIS PROCESS

CROSS-REFERENCE TO RELATED APPLICATIONS

This application is the national phase of, and claims priority to, International Patent Application No. PCT/EP2014/003315, filed Dec. 11, 2014, which designated the U.S. and which claims priority to German Patent Application Number DE 10 2013 113 980.9, filed Dec. 12, 2013. Each of these applications is incorporated by reference herein in its entirety.

BACKGROUND

1. Field of the Invention

The invention relates to a process for preparing ammonia and $CO_2$ for urea synthesis.

2. Description of Related Art

Industrially, urea is obtained from $NH_3$ and $CO_2$ via the intermediate ammonium carbamate. The ammonium carbamate is formed rapidly and completely when dissociation is avoided by means of a sufficiently high reaction pressure. The exothermically formed ammonium carbamate is converted endothermically into urea in subsequent decomposition stages at low pressure, with excess gases being able to be recirculated back to the reactor. The reaction to form ammonium carbamate is carried out using an excess of $NH_3$, with a molar ratio of $NH_3/CO_2$ of about 4 frequently being selected in practice.

Raw materials for the urea synthesis are $CO_2$ and $NH_3$. Since carbon dioxide is obtained as a secondary component in the synthesis of ammonia, a urea plant is frequently operated in conjunction with an ammonia plant. Plants which ultimately produce urea from natural gas synthesize ammonia from natural gas and air, and then synthesize urea from this ammonia and carbon dioxide.

SUMMARY

In view of the background above, it is an object of the invention to provide an efficient process for producing the gaseous starting materials for urea synthesis. To operate the process, a raw gas which is obtained as a waste product in an industrial process should be utilized. The raw gas and the process steps should be selected so that the gas components of the raw gas are substantially completely converted into ammonia and $CO_2$ in the proportions necessary for the urea synthesis.

BRIEF DESCRIPTION OF THE DRAWING

The FIGURE is a schematic block diagram illustrating a process for preparing gaseous starting materials for synthesis of urea.

DETAILED DESCRIPTION

According to the invention, a metallurgical gas which contains blast furnace gas at least as a mixing component, or which consists of blast furnace gas, is used for preparing the gaseous starting materials for urea synthesis. Blast furnace gas is obtained in the production of pig iron in a blast furnace. In the blast furnace, pig iron is obtained from iron ores, additives, and coke and other reducing agents such as coal, oil or gas. As products of the reduction reactions, $CO_2$, hydrogen and water vapor are inevitably formed. A blast furnace gas taken from the blast furnace process has, in addition to the abovementioned constituents, a high content of nitrogen. The composition of the blast furnace gas is dependent on the feedstocks and the mode of operation, and is subject to fluctuations. However, blast furnace gas usually contains from 35 to 60% by volume of $N_2$, from 20 to 30% by volume of CO, from 20 to 30% by volume of $CO_2$ and from 2 to 15% by volume of $H_2$.

Furthermore, a metallurgical gas which consists of a mixed gas composed of blast furnace gas and converter gas, or of a mixed gas composed of blast furnace gas, converter gas and coke oven gas can be used for the process of the invention. Converter gas, which is created from pig iron during the steel production process, has a high content of CO, and also contains nitrogen, hydrogen and $CO_2$. A typical converter gas composition has from 50 to 70% by volume of CO, from 10 to 20% by volume of $N_2$, about 15% by volume of $CO_2$ and about 2% by volume of $H_2$. Coke oven gas is obtained in the coking of coal and has a high hydrogen content and appreciable amounts of $CH_4$. Coke oven gas typically contains from 55 to 70% by volume of $H_2$, from 20 to 30% by volume of $CH_4$, from 5 to 10% by volume of $N_2$ and from 5 to 10% by volume of CO. The coke oven gas additionally comprises $CO_2$, $NH_3$ and $H_2S$.

In the process of the invention, a process gas containing nitrogen, hydrogen and carbon dioxide as main components is produced from the metallurgical gas and this process gas is subsequently fractionated to give a gas stream containing the $CO_2$ component and a gas mixture consisting primarily of $N_2$ and $H_2$. An ammonia gas suitable for the urea synthesis is produced from the gas mixture by means of ammonia synthesis. $CO_2$ is branched off from the $CO_2$-containing gas stream in a purity and amount suitable for the urea synthesis. The conditioning of the metallurgical gas and the separation steps described can be matched to one another in such a way that ammonia and $CO_2$ are formed in the proportions necessary for the urea synthesis and the metallurgical gas can be utilized almost completely for preparing the gaseous starting materials required for the urea synthesis.

The use of the metallurgical gas for producing process gas is advantageously preceded by a gas purification process. The gas purification process serves to separate undesirable constituents, in particular tar, sulfur and sulfur compounds, aromatic hydrocarbons (BTX) and high-boiling hydrocarbons.

The CO component of the metallurgical gas can be converted into $CO_2$ and $H_2$ by means of a water gas shift reaction, forming a process gas which contains nitrogen, hydrogen and carbon dioxide as main components.

The process gas is subsequently fractionated, preferably by means of pressure swing adsorption (PSA), to give a gas mixture consisting primarily of nitrogen and hydrogen and an offgas, also referred to as PSA offgas, containing the $CO_2$ component. Pressure swing adsorption (PSA), which is known in the prior art, is used for the isolation and purification of hydrogen. In the context of the process of the invention, the pressure swing adsorption is operated in combination with a preceding gas conditioning process in such a way that a desired concentration ratio of $H_2$ and $N_2$ is established. One aspect of the process of the invention is therefore the coupling of a gas conditioning process, in particular a water gas shift reaction, with a pressure swing adsorption in order to produce a synthesis gas suitable for the ammonia synthesis from metallurgical gas which contains blast furnace gas at least as a mixing component, or which consists of blast furnace gas. Furthermore, secondary components which are unfavorable for the ammonia synthesis, e.g. argon, methane or carbon monoxide, can be removed or have their concentrations reduced by means of the pressure swing adsorption.

The pressure swing adsorption produces an energy-rich offgas (PSA offgas) which contains the $CO_2$ component of the process gas and any residual proportions of CO. $CO_2$ for the urea synthesis is obtained from the PSA offgas. In a preferred embodiment of the process of the invention, the $CO_2$ component is separated from the pressure swing adsorption offgas (PSA offgas) and is subsequently separated into a gas containing a high concentration of $CO_2$ for the urea synthesis and a tailgas having a lower concentration of $CO_2$.

The invention also provides a process for preparing urea, in which ammonium carbamate is produced from ammonia gas and $CO_2$ using an excess of ammonia and this ammonium carbamate is dissociated into water and urea. According to the invention, the ammonia gas required for the synthesis of urea and the $CO_2$ which is likewise required for the synthesis of urea are each produced from a metallurgical gas which contains blast furnace gas at least as a mixing component, or which consists of blast furnace gas. It is essential for the process of the invention, according to an embodiment, that the gaseous starting materials for the urea synthesis are obtained entirely from the metallurgical gas. The gaseous starting materials for the urea synthesis are obtainable by the process described further above.

The invention will be illustrated below with reference to the FIGURE, which depicts merely one working example. The single FIGURE schematically shows, in the form of a greatly simplified block diagram, a process for preparing gaseous starting materials for a urea synthesis.

A process gas 2 containing nitrogen ($N_2$), hydrogen ($H_2$) and carbon dioxide ($CO_2$) as main components is produced from a metallurgical gas 1 which contains blast furnace gas at least as a mixing component and in the working example consists of blast furnace gas by means of the process depicted in the FIGURE.

The blast furnace gas 1 has, for example, a typical composition of 50% by volume of $N_2$, 24% by volume of $CO_2$, 21% by volume of CO and about 4% by volume of $H_2$. After a gas purification process 3 in which undesirable constituents, for example tar, sulfur and sulfur compounds, aromatic hydrocarbons (BTX) and high-boiling hydrocarbons are separated, the metallurgical gas 1 consisting of blast furnace gas is converted by means of a gas conditioning process 4 into the process gas 2 which consists mainly of $N_2$, $H_2$ and $CO_2$. The gas conditioning process 4 includes, in particular, a CO conversion in which the CO component of the metallurgical gas 1 is converted into $CO_2$ and $H_2$ by means of a water gas shift reaction:

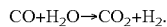
$$CO+H_2O \rightarrow CO_2+H_2.$$

After the conversion or the water gas shift reaction, the process gas has a composition of about 37% by volume of $CO_2$, 21% by volume of $H_2$ and 42% by volume of $N_2$.

The process gas 2 is fractionated by means of pressure swing adsorption (PSA) 16 to give a gas mixture 5 consisting primarily of $N_2$ and $H_2$ and an offgas 6 containing the $CO_2$ component. An ammonia gas 8 suitable for the synthesis of urea is produced from the $N_2$— and $H_2$-containing gas mixture by means of an ammonia synthesis 7. In the ammonia synthesis 7, the gas mixture composed of hydrogen and nitrogen can, for example, be reacted over an iron oxide mixed catalyst at pressures in the range from 150 to 200 bar and at a reaction temperature of from 350 to 550° C.

$CO_2$ for the urea synthesis 9 is obtained from the offgas 6 from the pressure swing adsorption. According to the process scheme depicted in the FIGURE, the $CO_2$ component 11 is separated from the offgas 6 from the pressure swing adsorption in a first separation stage 10. Subsequently, a separation into a gas 13 containing a high concentration of carbon dioxide and a tailgas 14 having a low concentration of $CO_2$ is carried out in a second separation stage 12. The gas 13 is, in particular, carbon dioxide in a purity necessary for the urea synthesis.

$CO_2$ and $NH_3$ are fed to the urea plant in the proportions required for the urea synthesis 9. In the urea plant, ammonium carbamate is produced using an excess of ammonia and this ammonium carbamate is converted into urea 15 in subsequent decomposition stages at low pressure.

The process illustrated in the FIGURE can also be operated using a gas mixture of blast furnace gas and converter gas or using a gas mixture of blast furnace gas, converter gas and coke oven gas as metallurgical gas 1.

The invention claimed is:

1. A process for preparing ammonia gas and $CO_2$ for a urea synthesis, comprising:
   producing a process gas containing nitrogen, hydrogen, and carbon dioxide as main components from a metallurgical gas comprising a mixed gas composed of blast furnace gas and converter gas;
   fractionating the process gas to give a first gas containing carbon dioxide and a second gas mixture consisting essentially of nitrogen and hydrogen;
   producing an ammonia gas suitable for the urea synthesis directly from the second gas mixture by means of ammonia synthesis;
   branching off carbon dioxide from the first gas in a purity and amount suitable for the urea synthesis; and
   carbamate from the ammonia gas and carbon dioxide suitable for the urea synthesis,
   wherein:
      the branching step comprises:
         a first separation stage, wherein a carbon dioxide-enriched gas stream is separated from the first gas; and
         a second separation stage, wherein the carbon dioxide-enriched gas stream from the first separation stage is separated into a third gas stream comprising carbon dioxide suitable for urea synthesis, and a tailgas.

2. The process as claimed in claim 1, wherein the metallurgical gas consists of a mixed gas composed of blast furnace gas, converter gas and coke oven gas.

3. The process as claimed in claim 1, wherein the metallurgical gas is purified before being used for producing the process gas.

4. The process as claimed in claim 1, wherein the metallurgical gas contains a carbon monoxide component, and wherein the carbon monoxide component of the metallurgical gas is converted into carbon dioxide and hydrogen by means of a water gas shift reaction.

5. The process as claimed in claim 1, wherein the process gas is fractionated by means of pressure swing adsorption to give the first gas and the second gas mixture.

6. The process as claimed in claim 5, further comprising:
conditioning the process gas to produce a conditioned process gas comprising nitrogen and hydrogen in a concentration ratio suitable for ammonia synthesis;
wherein the conditioning process occurs prior to the fractionating step; and
wherein the conditioned process gas is fractionated in the fractionating step to give the first gas and the second gas mixture.

7. A process for preparing ammonia gas and carbon dioxide for a urea synthesis, comprising:
producing a process gas containing nitrogen, hydrogen, and carbon dioxide as main components from a metallurgical gas comprising a mixed gas composed of blast furnace gas and converter gas;
fractionating the process gas by means of pressure swing adsorption to give a first gas stream containing the carbon dioxide and a second gas mixture consisting essentially of $N_2$ and $H_2$,
producing an ammonia gas suitable for the urea synthesis directly from the second gas mixture by means of ammonia synthesis;
branching off carbon dioxide from the first gas stream in a purity and amount suitable for the urea synthesis; and
synthesizing the urea via an intermediate ammonium carbamate from the ammonia gas and carbon dioxide suitable for the urea synthesis,
wherein:
the branching step comprises:
a first separation stage, wherein a carbon dioxide-enriched gas stream is separated from the first gas stream; and
a second separation stage, wherein the carbon dioxide-enriched gas stream from the first separation stage is separated into a third gas stream comprising carbon dioxide suitable for urea synthesis, and a tailgas;

wherein:
the blast furnace gas has 35-60% by volume nitrogen and 20-30% by volume of each of carbon dioxide and carbon monoxide.

8. A process for preparing ammonia gas and carbon dioxide for a urea synthesis, comprising:
producing a process gas containing nitrogen, hydrogen, and carbon dioxide as main components from a metallurgical gas comprising a mixed gas composed of blast furnace gas and converter gas;
fractionating the process gas by means of pressure swing adsorption to give a first gas stream containing the carbon dioxide and a second gas mixture consisting essentially of nitrogen and hydrogen;
producing an ammonia gas suitable for the urea synthesis directly from the second gas mixture by means of ammonia synthesis;
branching off the carbon dioxide from the first gas stream in a purity and amount suitable for the urea synthesis;
the branching step comprising:
a first separation stage, wherein a $CO_2$-enriched gas stream is separated from the first gas stream; and
a second separation stage, wherein the $CO_2$-enriched gas stream from the first separation stage is separated into a third gas stream comprising carbon dioxide suitable for urea synthesis, and a tailgas; and
carbamate from the ammonia gas and carbon dioxide suitable for the urea synthesis,
wherein:
the blast furnace gas has 50% by volume nitrogen, 24% by volume carbon dioxide, and 21% by volume carbon monoxide.

9. The process of claim 8, wherein the converter gas has 50-70% by volume carbon monoxide, 10-20% by volume nitrogen, and about 15% by volume carbon dioxide.

* * * * *